United States Patent
Lomenzo

(10) Patent No.: US 8,505,384 B2
(45) Date of Patent: Aug. 13, 2013

(54) RIG FOR MEASURING BLADED COMPONENT MISTUNING

(75) Inventor: Richard A. Lomenzo, Enfield, CT (US)

(73) Assignee: United Technologies Corporation, Hartford, CT (US)

( * ) Notice: Subject to any disclaimer, the term of this patent is extended or adjusted under 35 U.S.C. 154(b) by 198 days.

(21) Appl. No.: 13/022,651

(22) Filed: Feb. 8, 2011

(65) Prior Publication Data

US 2012/0198938 A1    Aug. 9, 2012

(51) Int. Cl.
*G01M 7/00* (2006.01)

(52) U.S. Cl.
USPC .............................................. 73/655; 73/649

(58) Field of Classification Search
USPC ............. 73/649, 593, 655, 662, 663; 702/39, 702/56
See application file for complete search history.

(56) References Cited

U.S. PATENT DOCUMENTS

| | | | | |
|---|---|---|---|---|
| 4,070,762 | A * | 1/1978 | Siddall | 33/504 |
| 5,402,681 | A * | 4/1995 | Nakaso et al. | 73/602 |
| 6,629,463 | B2 * | 10/2003 | Naudet et al. | 73/579 |
| 7,082,371 | B2 * | 7/2006 | Griffin et al. | 702/56 |
| 7,383,136 | B1 | 6/2008 | Griffin et al. | |
| 7,443,513 | B2 | 10/2008 | Rembe | |
| 7,497,664 | B2 * | 3/2009 | Walter et al. | 416/223 A |
| 8,024,137 | B2 * | 9/2011 | Kuehhorn et al. | 702/56 |
| 8,197,207 | B2 * | 6/2012 | Petersen et al. | 416/61 |
| 2010/0286934 | A1 | 11/2010 | Kuehhorn et al. | |

* cited by examiner

*Primary Examiner* — J M Saint Surin
(74) *Attorney, Agent, or Firm* — Carlson, Gaskey & Olds, PC

(57) ABSTRACT

A rig for studying a component has a component support for mounting the component. A speaker applies sound energy to airfoils in the component. A vibrometer studies the effect of the applied sound on the airfoils. At least two of the vibrometer, the component support, and the speaker are rotatable relative to each other. In a separate feature, a vibrometer for studying the effect of sound energy on airfoils in a component is provided with a vision system. The vision system is operable to identify the exact location at which the laser is studying the effect on the airfoil. Methods are also disclosed.

20 Claims, 2 Drawing Sheets

RIG FOR MEASURING BLADED COMPONENT MISTUNING

BACKGROUND

This application relates to a rig including a speaker, and a measurement system.

Integrally bladed rotors ("IBRs") are known, and typically include a hub with a plurality of airfoil blades extending outwardly of the hub. These IBRs are often utilized in gas turbine engines as part of the fan section, and sometimes the compressor and even turbine sections.

It is important to test the IBR to ensure that it is properly constructed. As an example, IBRs may experience different blade dynamic response in an engine due to a variety of phenomena.

One particular phenomena is called mistuning, and comes about due to a difference in blade-to-blade geometries and frequencies when system energy is coupled through the IBR structure and shared unequally by the airfoils of the IBR. It is known to have a traveling wave evaluation system that moves a laser vibrometer to predefined spots on the airfoil while exciting the IBR in conditions that would be relevant to engine operation via an array of speakers. Vibrometer data is then utilized to assess the IBR mistuning risk prior to accepting an IBR as a quality control measure, and also initially to approve a design of a new IBR product configuration.

The current system utilizes a "on-axis" vibrometer system. An IBR is rotated about an axis of rotation, and in the vision path of a vibrometer located over that rotational axis. The laser has mirrors that allows movement of its beam about the tips of blades on the IBR. The beam is positioned on the tip of a blade. A speaker is moved under that blade, and a sound energy is applied to one blade. The laser then indexes to measure every other blade, based upon the sound energy put into each blade. Reflective tape is positioned on each blade to provide a target for the laser.

While the above system works well for large IBRs, smaller IBRs raise challenges, and in particular, might have responses at higher frequencies and require greater measurement accuracy. In addition, the surface preparation, such as the tape, is somewhat burdensome.

SUMMARY

A rig for studying a component has a component support for mounting the component. A speaker applies sound energy to airfoils in the component. A vibrometer studies the effect of the applied sound on the airfoils. At least two of the vibrometer, the component support, and the speaker are rotatable relative to each other.

In a separate feature, a vibrometer for studying the effect of sound energy on airfoils in a component is provided with a vision system. The vision system is operable to identify the exact location at which the laser is studying the effect on the airfoil.

Methods are also disclosed and claimed.

These and other features of the present invention can be best understood from the following specification and drawings, of which the following is a brief description.

DETAILED DESCRIPTION

Figure 1:
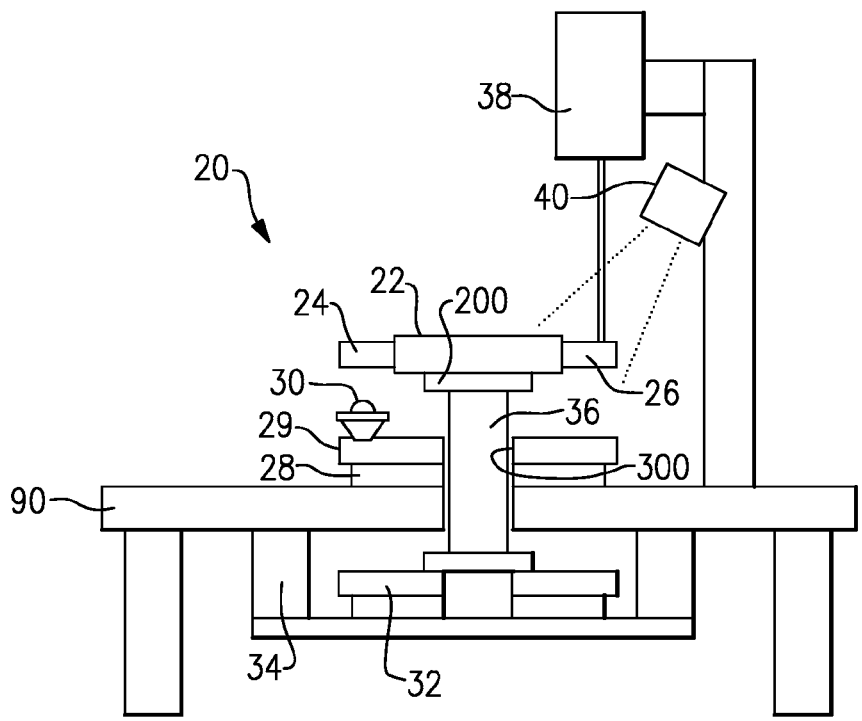
FIG. 1 shows a rig in a first configuration.

A rig 20 is illustrated in FIG. 1. An IBR 22 is illustrated on a support or platform 36. Two blades 24 and 26 of the IBR are illustrated. It should be understood that the IBR would typically be provided with a greater number of blades.

A rotating table 28 supports a speaker 30. A rig 29 allows the location of the speaker 30 to be changed in a radial direction about an axis of rotation of the table 28.

The support 36 extends to a rotary table 32. The rotary table 32 is supported on a movable fixture 34 that allows the distance between the tables 28 and 32 to be adjusted relative to a fixed support 90.

A vibrometer 38 and a vision system 40 are utilized to evaluate the effect of sound from the speaker 30 on the blades 24 or 26. The speaker 30 is utilized to apply a vibration or sound frequency into the blades 24 and 26, and the vibrometer 38 and vision system 40 act to evaluate the effect.

The interpretation of the data gathered by the vision system 40 or the vibrometer 38 is as known. Notably, the prior art has not utilized a vision system to provide feedback of the exact location. However, once the exact location is known, the processing of the data to identify whether a particular design or IBR is as desired may be similar to the known art. The new system will generate a somewhat different data set, however, the data is generally processed as known. As an example, the prior system would have a different number of data files than that generated by the new system.

Vibrometer 38 is positioned to be perpendicular to the blades 26/24 but spaced from a rotational axis of tables 28 and 32. The vision system 40 is able to identify the exact location where the beam is applied to the blade. This provides a powerful ability to know precisely where on the blade the vibration is measured. Known vision systems, such as a white light inspection system, or Capture 3-DATOS may be utilized. The vision system can identify the edge and the geometry, and know exactly where the laser beam from the vibrometer is spotted. Generally, any high resolution vision system may be utilized.

With the present off-axis arrangement, the part and the speaker rotate relative to the vibrometer 38. In a disclosed embodiment, the speaker is placed under one blade, with that blade in view of the laser. Sound energy is applied, and the effect determined. The speaker is then moved under a second blade, but the vibrometer 38 still evaluates the effect on blade one. At the end of this process, the IBR 22 is then indexed such that the vibrometer can study the effect on a second blade as the speaker indexes across all of the other blades. As is known, the vibrometer generally measures motion of the blade due to the sound energy. Frequency and amplitude generally based upon "Doppler effect" provides feedback to a designer as to any mistuning in the particular IBR.

The support 36 has an upper surface 200 which includes positioning members to ensure the IBR is positioned at a desired location relative to an axis of rotation, and thus at a known position relative to the vibrometer 38 and vision system 40. As is also clear in FIG. 1, a rotational axis of the rotary table 32, and the rotating table 28 are common. In addition, the support 36 extends through a central opening 300 in the table 28. In this manner, the location of the speaker 30, and the blades 24/26 on the IBR can be easily adjusted to an infinite number of relative rotational positions. In a broad aspect of this concept, the location of at least two of the vibrometer 38 and vision system 40 combination, the IBR 22, and the speaker 30, can be rotated relative to the third. In the disclosed embodiment, it is the location of the IBR 22 and speaker 30 which are each independently rotatable relative to the combination of vibrometer 38 and vision system 40.

Figure 2:
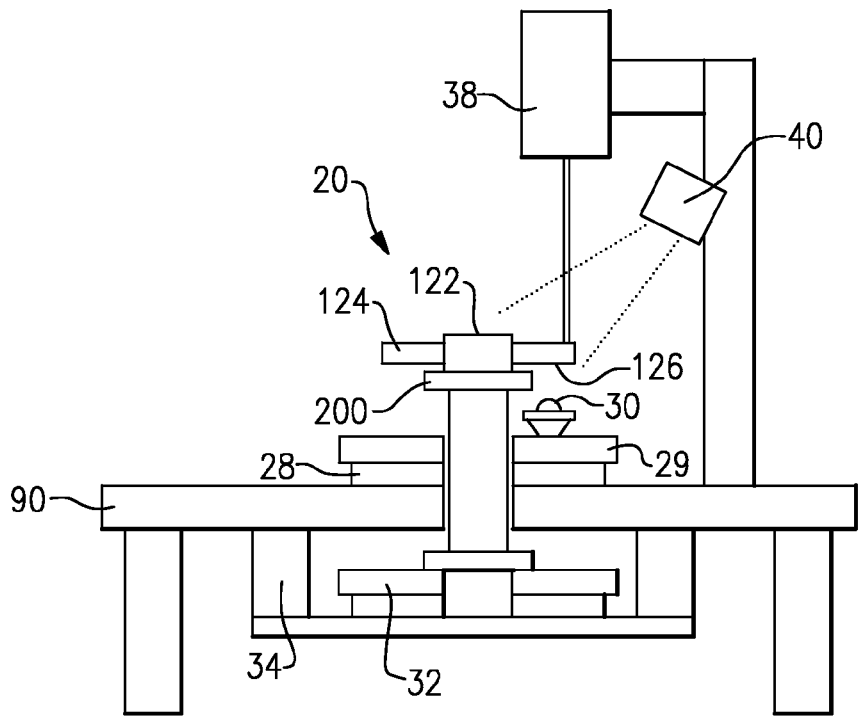
FIG. 2 shows the rig arranged for a different configuration.

FIG. 2 shows an adjusted position wherein the radial position and rotational position of the speaker 30 has been adjusted. Again, the rig 29 allows the speaker 30 to be mounted at any number of radial locations. The rotating table 28 has rotated the speaker such that it is now underneath the blade 126. Again, the vibrometer 38 and vision system 40 are utilized to gather data. In one embodiment, the vibrometer 38 is positioned such that its beam will be perpendicular to surfaces on the blade 126, which may simplify surface preparation. This facilitates the evaluation of a smaller IBR than the FIG. 1 position.

Figure 3:
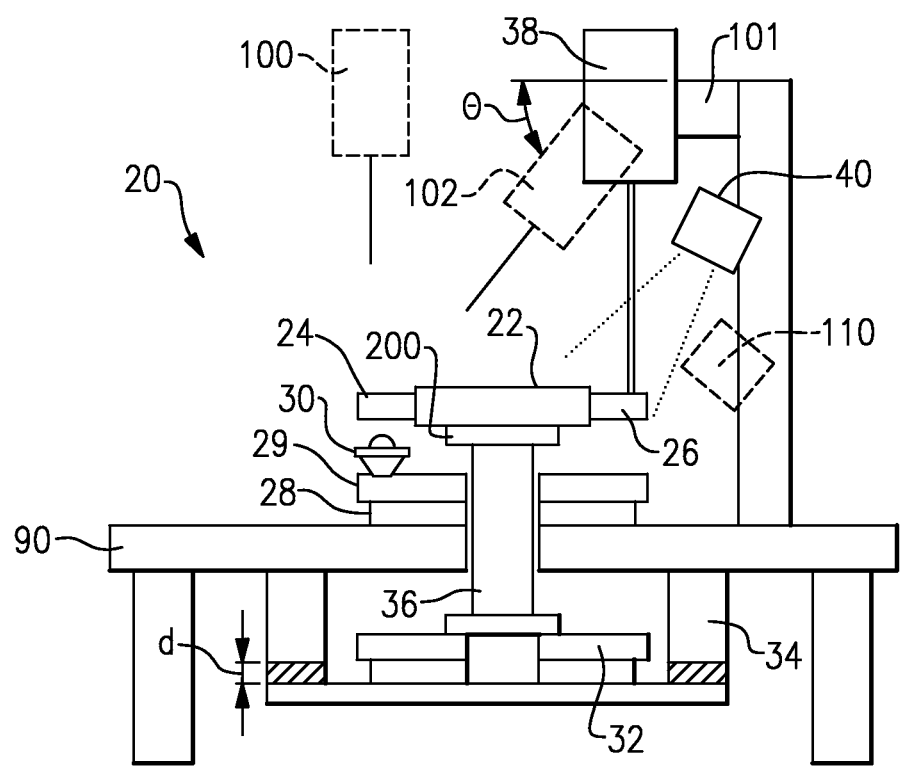
FIG. 3 shows yet another configuration.

FIG. 3 shows a number of other adjustments. As shown, the slide structure or fixture 34 has now moved the table 32 downwardly in this view such that the blade 24 is now closer to the speaker 30. Again, a worker of ordinary skill in the art would recognize when this would be valuable.

In addition, the vibrometer 38 may be adjusted axially relative to a fixed support 101. As shown in outline at 100, the vibrometer 38 has been moved to a position on an opposed side of the axial center of rotation of the table 32. In addition, an angle of the vibrometer may be adjusted as shown at 102 such that the beam is not necessarily perpendicular to the blade any longer. This will assist the vibrometer in being able to gather information from a number of locations of blades 24 and 26. In addition, the relative axial position of the vibrometer 38 and vision system 40 may be adjusted, such as shown at 110 in phantom.

Again, a worker of ordinary skill in this art would recognize when each of these modifications would be valuable. The structure to allow adjustment may be any known structure.

The combined rig allows relatively small IBRs to be studied at very high frequencies. Also, while the rig is disclosed specifically utilized with IBRs, it should be understood that the rig could be utilized with any component with airfoils. As an example, integrally bladed part sections, such as a multiple vane section, for example, can benefit from this invention. In addition, rotors, which have removable blades can also be evaluated. To that end, broadly, the rig and methods as disclosed above could be utilized to evaluate any component with an airfoil.

Although an embodiment of this invention has been disclosed, a worker of ordinary skill in this art would recognize that certain modifications would come within the scope of this invention. For that reason, the following claims should be studied to determine the true scope and content of this invention.

What is claimed is:

1. A rig for studying a component with airfoils including:
   a component support for mounting and rotating a component about an axis;
   a speaker to apply sound energy to airfoils in the component;
   a vibrometer positioned off said axis, and for studying the effect of the applied sound on the airfoils; and
   wherein at least two of the vibrometer, the component support, and the speaker are rotatable relative to each other.

2. The rig as set forth in claim 1, wherein the speaker is mounted on a speaker rotating table.

3. The rig as set forth in claim 2, wherein a radial location of the speaker is adjustable relative to a rotational axis of the speaker rotating.

4. The rig as set forth in claim 2, wherein the component support also rotates about a common axis with the speaker rotating table.

5. The rig as set forth in claim 4, wherein the component support has a portion extending through a center opening in the speaker rotating table.

6. The rig as set forth in claim 1, wherein a position of the vibrometer is adjustable along a dimension in a plane perpendicular to said axis.

7. The rig as set forth in claim 1, wherein a vision system is combined with the vibrometer to identify the location of a beam from the vibrometer on each airfoil.

8. The rig as set forth in claim 7, wherein said vision system is a high resolution vision system.

9. The rig as set forth in claim 1, wherein the component is an integrally bladed rotor.

10. A rig for studying a component with airfoils including:
    a component support for mounting and rotating a component about an axis;
    a speaker to apply sound energy to airfoils in the component;
    a vibrometer and vision system combination, with said vibrometer applying a beam to said airfoils to measure the effect of the applied sound energy on said airfoils, and said vision system identifying the location of said beam on each said airfoil.

11. The rig as set forth in claim 10, wherein said vision system is a high resolution vision system.

12. The rig as set forth in claim 10, wherein the component support is operable to rotate about a central axis, and a beam from said vibrometer is positioned to be directed perpendicularly at an airfoil, and said beam is positioned to be spaced from the axis of rotation.

13. A method of studying a component with airfoils comprising the steps of:
    (a) mounting a component to be studied for rotation about an axis;
    (b) applying sound energy to airfoils in the component;
    (c) a vibrometer studying the effect of the applied sound on the airfoils;
    (d) rotating at least two of the vibrometer, the component, and the speaker relative to each other, and wherein a beam from the vibrometer is mounted to be directed perpendicularly at the airfoil, with the beam being positioned to be spaced from an axis of rotation of the component.

14. The method as set forth in claim 13, wherein the speaker is rotated.

15. The method as set forth in claim 14, wherein a radial location of the speaker relative to a rotational axis of the speaker is adjusted.

16. The method as set forth in claim 14, wherein a support for the component rotates about a common axis with the speaker.

17. The method as set forth in claim 16, wherein a position of the vibrometer along a dimension in a plane perpendicular to said axis is adjusted.

18. The method as set forth in claim 13, wherein a vision system gathers data of a location where a beam from the vibrometer is directed to on an airfoil.

19. The method as set forth in claim 13, wherein the component with airfoils is a bladed rotor.

20. The method as set forth in claim 19, wherein the component is an integrally bladed rotor.

* * * * *